US006824739B1

(12) United States Patent
Arney et al.

(10) Patent No.: US 6,824,739 B1
(45) Date of Patent: Nov. 30, 2004

(54) OXIDATION SENSOR FOR AN ELECTRICAL CIRCUIT AND A METHOD OF MANUFACTURE THEREFOR

(75) Inventors: Susanne Arney, Highland Park, NJ (US); David J. Bishop, Summit, NJ (US); Herbert R. Shea, Summit, NJ (US)

(73) Assignees: Agere Systems Inc., Allentown, PA (US); Lucent Technologies Inc., Murray Hill, NJ (US)

( * ) Notice: Subject to any disclaimer, the term of this patent is extended or adjusted under 35 U.S.C. 154(b) by 366 days.

(21) Appl. No.: 09/706,274

(22) Filed: Nov. 3, 2000

(51) Int. Cl.[7] .................... G01N 27/27; G01N 27/416
(52) U.S. Cl. .............................. 422/82.01; 422/82.02; 422/98; 436/149; 436/151; 204/401; 204/404; 204/406
(58) Field of Search ............................. 422/68.1, 82.01, 422/82.02, 98; 436/149, 151; 204/401, 404, 406

(56) References Cited

U.S. PATENT DOCUMENTS

| 5,310,470 A | * | 5/1994 | Agarwala et al. ........... 204/404 |
| 5,548,224 A | * | 8/1996 | Gabriel et al. ............... 324/765 |

FOREIGN PATENT DOCUMENTS

| JP | 58-189548 | * 11/1983 |
| JP | 59-4102 | * 1/1984 |

OTHER PUBLICATIONS

Vaidya, S. et al, Annual Proceedings—Reliability Physics [Symposium] 1980, 18th, 165–170.*
Troyk, P. R. et al, International SAMPE Electronics Conference 1989, 3, 969–982.*
Gabriel, C. et al, Proceedings—Electrochemical Society 1994, 94–20, 281–290.*
Murphy, C. F. et al, Proceedings of SPIE 1994, 2256(Multichip Modules), 338–343.*
De Munari, I. et al, Quality and Reliability Engineering International 1995, 11, 1, 33–39.*
Agarwala, V. S. International Corrosion Congress, Proceedings, 13th, Melbourne, Nov., 1996, Paper 431/1–Paper 431/7 Publisher: Australasian Corrosion Association, Clayton, Australia.*
Gabriel, C. et al, Chemical Abstracts 1995, 122, abstract 175490z.*
Fabianowski, W. et al, Advanced Materials for Optics and Electronics 1995, 5, 199–213.*
Ziaie, B. et al, Journal of Microelectromechanical Systems 1996, 5, 166–179.*
Sbar, N. L. et al, Annu. Proc., Reliab. Phys. Symp. 1978, 16, 161–178.*

(List continued on next page.)

*Primary Examiner*—Arlen Soderquist

(57) ABSTRACT

The present invention provides an oxidation sensor for an electrical circuit or MEMS device that includes a conductor located on an insulating substrate and a sensor trace located on the insulating substrate adjacent the conductor. The sensor trace is located on the insulating substrate adjacent the conductor and is configured to oxidize at a rate greater than an electrical component associated with the sensor trace on the electrical circuit or MEMS device when the sensor trace and the electrical component are exposed to a same oxidizing environment. By oxidizing and thus becoming an open circuit more rapidly than any structure on a electrical circuit or MEMS device at a given relative humidity (i.e. in the same package), the oxidation sensor is designed to provide early warning of oxidation. Thus, the present invention serves as a sensor that will give advance warning of a leaky package and associated oxidation.

40 Claims, 11 Drawing Sheets

OTHER PUBLICATIONS

Lowry, R. K. NSB Special Publication 1982, 400–72, 64–75.*

Iannuzzi, M. Proceedings—Electronic Components Conference 1983, 33rd, 591–601.*

Lin, A. W. et al, Proceedings—Electronic Components & Technology Conference 1991, 41st, 820–826.*

Bargeron, C. B. et al, Proceedings—Electronic Components & Technology Conference 1991, 44th, 728–732.*

Sweet, J. N. Sandia Report SAND 1997, SAND97–1721, 1–35.*

Enlow, L. R. et al, SPIE 1997, 3235, 314–321.*

Foley, S. et al, IEEE International Reliability Physics Symposium Proceedings 1999, 37th, 213–220.*

M. L. White Proc. IEEE 1969, 57, 1610–1615.*

R. G. Manke IEEE Trans. Compon. Hybrids Manuf. Technol. 1981, CHMT–4, 492–498.*

R. K. Lowry Chem. Abstr. 1982, 97, abstract 64838q.*

O. Nakagawa et al, J. Electron. Mater. 1984, 13, 231–250.*

T. Wada et al, J. Electrochem. Soc. 1987, 134, 649–653.*

T. Wada et al, Electrochem. Soc. 1989, 136, 732–735.*

J. J. Burack et al, IEEE Trans. Compon. Hybrids Manuf. Technol. 1990, 13,214–218.*

K. M. Takahashi J. Appl. Phys. 1990, 67, 3419–3429.*

M. Kimura et al, Jpn. J. Appl. Phys. 1996, 35, 1478–1483.*

C. White et al, Proc. SPIE 2000, 4180, 91–95.*

H. R. Shea et al, Proc. SPIE 2000, 4180, 117–122.*

* cited by examiner

| %RH | 51 | 63 | 68 | 83 |
|---|---|---|---|---|
| Time to open Circuit (hours) | >48 | 3.5 | 1.5 | 0.9 |

OXIDATION SENSOR FOR AN ELECTRICAL CIRCUIT AND A METHOD OF MANUFACTURE THEREFOR

TECHNICAL FIELD OF THE INVENTION

The present invention is directed, in general, to an oxidation sensor for an electrical circuit and, more specifically, to a system to provide early warning of oxidation of surface micro-machined Poly-Si MEMS structures.

BACKGROUND OF THE INVENTION

Micro-electromechanical systems (MEMS) is a well known technology that combines microfabricated electrical circuits with microfabricated mechanical devices such as sensors, valves, gears, mirrors and actuators fabricated on or in semiconductor chips, and is an industry that is growing at an accelerating pace. A MEMS device contains microcircuitry on a tiny silicon chip into which a mechanical device such as a mirror has been manufactured. The mechanical device moves mechanically under the control of an electrical signal or the device is externally activated and the motion is detected electrically or optically. MEMS systems include systems such as spatial light modulators, deformable mirrors, steerable mirrors, shutters, micro-antennas, relays, and accelerometers. With the rapid commercialization of MEMS, their reliability is of great importance.

In the area of unpassivated MEMS devices, it is recognized that humidity can be an accelerating factor for most phenomenons that may detrimentally affect the devices. Because there is no protective covering on top of the poly-silicon electrodes and wires, they are packaged absolutely hermetically in order to protect the devices from unknown reliability issues.

To prevent the detrimental effects associated with humidity, the industry has designed various packaging systems to isolate the MEMS device from the humidity as much as possible. For example, the industry has developed hermetically sealed ceramic packages that contain the MEMS chip.

In some cases, the hermetically sealed ceramic package can become cracked or damaged sufficiently to allow moisture to enter the package. In such cases, the ingress of moisture within the package can result in operational failure of the device. Moisture may also come from sources inside the package, such as epoxies. The most well known failure phenomenon is stiction, which is the strong interfacial adhesion present between contacting surfaces.

Another failure phenomenon associated with humidity in MEMS devices is oxidation in mechanical systems. If microcracks exists in a system where there is a mechanical device made of silicon, a bit of native oxide can form inside the crack due to the presence of oxygen or water. Any kind of native oxidation, even at the Angstrom or nanometer level will cause a volume expansion inside the crack, which helps to drive the crack further and further into the silicon. The crack can not be closed because the oxide takes up twice the volume of the silicon it consumed. For these reasons, oxidation of silicon can contribute to mechanical reliability issues. This phenomenon has been demonstrated in fracture and fatigue of silicon parts.

Another problem associated with humidity is the reduction of the reflective coefficient of the metals used in optical MEMS devices. The mirrors used in optical MEMS devices are typically made up of a material that reflects light with high reflectivity at the desired wavelength of the light, for example at about the 1000–1600 nm wavelength range for the silicon dioxide optical fiber-based telecommunication systems. Some examples of such reflective materials are gold, silver, rhodium, platinum, copper or aluminum. These reflective metal films are deposited on a movable membrane substrate such as a silicon substrate. Optically, if you have a metal that is subject to tarnishing, then oxidation or moisture can lead to reducing the reflective coefficient of the metal. The reduction of the reflective coefficient of the metal in turn results in the inability to operate the device at its optimum capacity.

Accordingly, what is needed in the art is a system to provide early warning of system failure of polysilicon structures, thereby allowing the operator to replace the leaky package before device failure due to humidity-induced failure phenomena.

SUMMARY OF THE INVENTION

To address the above-discussed deficiencies of the prior art, the present invention provides an oxidation sensor for an electrical circuit or MEMS device that includes a conductor located on an insulating substrate and a sensor trace located on the insulating substrate adjacent the conductor. The sensor trace is located on the insulating substrate adjacent the conductor and is configured to oxidize at a rate greater than an electrical component that is associated with the sensor trace when the sensor trace and the electrical component are exposed to a same oxidizing environment. By oxidizing and thus becoming an open circuit more rapidly than any structure on a chip at a given relative humidity, the oxidation sensor is designed to provide early warning of oxidation. Thus, the present invention serves as a sensor that will give advance warning of a leaky or outgassing package and associated oxidation.

The foregoing has outlined, rather broadly, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention in its broadest form.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1A:
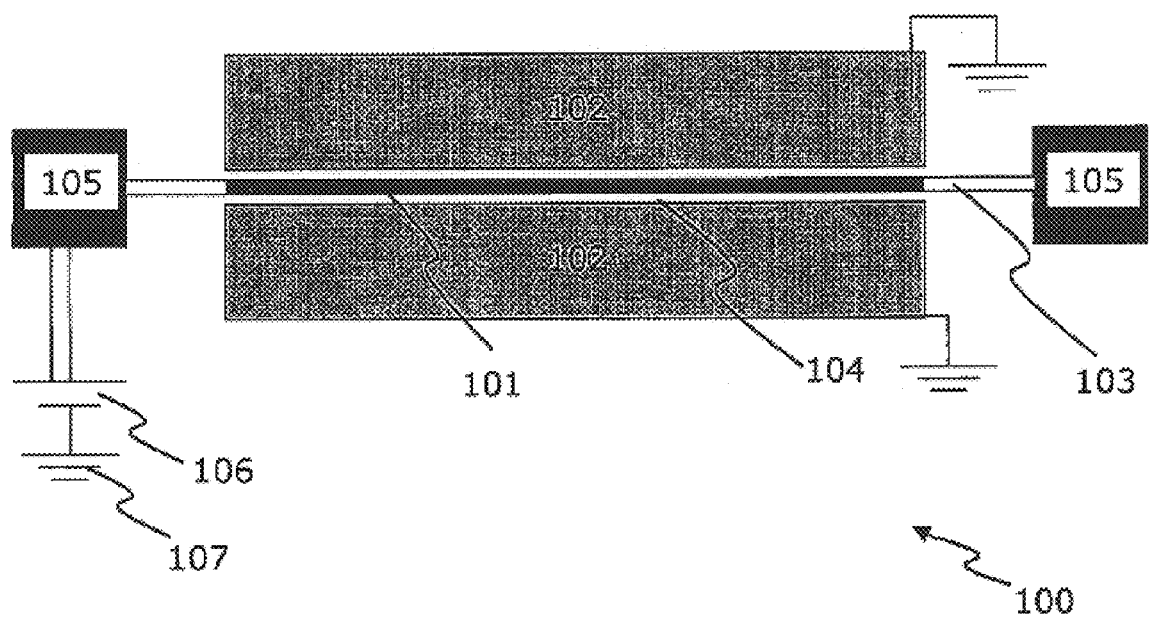
FIG. 1A illustrates a top view of an oxidation sensor of the present invention.
Figure 1B:
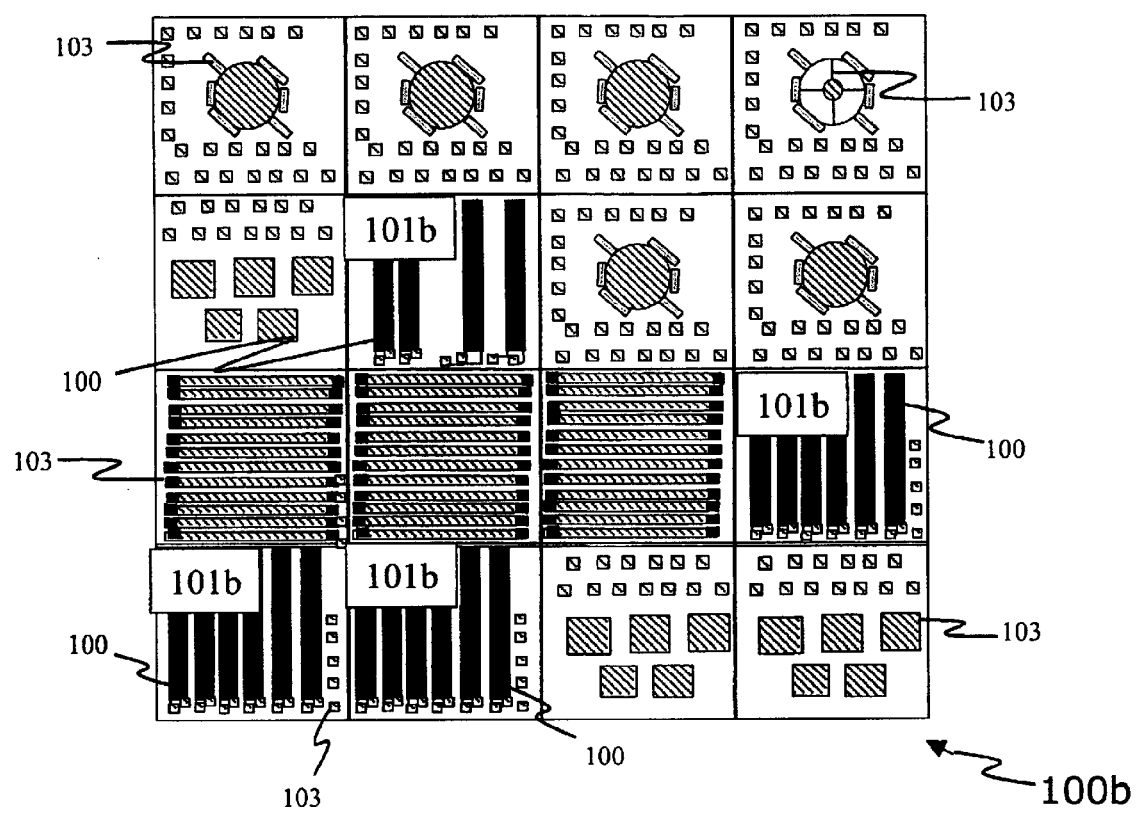
FIG. 1B illustrates a top view of a chip containing several sub-chips, 4 of which contain oxidation sensors.

Referring to FIG. 1A, illustrated is a top view of an oxidation sensor 100 for an electrical circuit, such as one that might be associated with an micro-electromechanical system (MEMS), constructed according to the principles of the present invention, which includes conductors 102 located on an insulating substrate and a sensor trace 101 located on the insulating substrate adjacent the conductor 102. An electrical component 103 will typically be associated with the sensor trace 101. For example, the electrical component 103 may be a conductive trace in adjacent electrical circuits or MEMS devices located on the same circuit board, chip or on another chip in the same package. An electrical component 103 is associated with the sensor trace 101 when the electrical component 103 is, for example, located within the same package, such that oxidation of the sensor trace 101 gives advanced warning of oxidation of the electrical component 103. In a broader sense, it should be understood that the electrical component 103 may be any electrical component or device that is associated with the sensor circuit 101 that is susceptible to oxidation when subjected to the substantially same environment as the sensor trace 101, such that oxidation of the sensor trace 101 gives advanced warning of oxidation of the electrical component 103. An exemplary embodiment which illustrates one such association is shown in FIG. 1B, where the electrical component 103 may be any component on the same circuit board or within the same package. FIG. 1B illustrates 4 subchips 101b that are located within a chip 100b. Within subchips 101b, there may be any number of oxidation sensors 100. For example, with respect to a MEMS device, there may be several MEMS chips and only one oxidation sensor 100, or one MEMS chip and several oxidation sensors 100 in a package.

In an advantageous embodiment, the sensor trace 101 is located between the conductors 102, and when in the presence of an applied voltage, the sensor trace 101 has a positive potential that is greater than a potential of the conductor 102. The sensor trace 101 is configured, as explained below, to oxidize at a rate greater than the electrical components 103 on adjacent electrical circuits or MEMS devices when exposed to the same oxidizing environment. In one advantageous embodiment, the sensor trace 101 comprises silicon because of its electrical and mechanical properties as well as its relative ease of processing in devices such as surface micromachined MEMS. The sensor trace 101 may comprise a conductive material selected from a number of conductive materials including titanium, copper, tungsten, aluminum, and tantalum. In one advantageous embodiment, the sensor trace 101 has a serpentine configuration, which allows the sensor trace 101 to have as long a length as possible, given design and restricted space parameters. A longer sensor trace 101 makes for a more sensitive sensor trace 101 with respect to oxidation.

As discussed previously, the MEMS chip typically consists of mechanical components and electrical circuits or wires. One common material for the wires is unpassivated poly-silicon. The MEMS chip normally operates in an ultra-dry ambient in a hermetically sealed package. In the case where a MEMS chip package is no longer hermetic as a result of moisture ingress or outgassing of moisture in the package, several failure phenomena may result. As discussed previously, stiction and oxide growth in microcracks are two failure phenomena associated with humidity.

However, another problem, which has previously been unrecognized for MEMS devices is anodic oxidation of electrical components 103 in the MEMS device, which in itself may be a failure phenomenon if it is left to transpire in the package for a long period of time. Anodic oxidation has recently been found to occur when moisture is present and there is a finite leakage current between neighboring poly-silicon electrodes or wires held a different electrical potential on the surface of the insulator. While the anodic oxidation was recently reported on polysilicon traces, it can also occur on any oxidizable conductor, such as aluminum, copper, etc. As the silicon is oxidized, it changes from conductive poly-silicon to insulating silicon oxide. That is, more and more conductive wire is replaced by insulating silicon dioxide. When the insulating silicon dioxide consumes the entire wire, then it becomes an insulator entirely. In other words, if the silicon is anodically oxidized long enough, the silicon ceases to be a conductor and becomes an open circuit. Once a wire becomes an open circuit, the electrode it drives becomes non-functional. Anodic oxidation of wires and electrodes can eventually lead to open circuits, as well as to gradual changes in the capacitance between electrical structures. Consequently, if moisture is introduced into the system the MEMS chip can eventually fail either from anodic oxidation of the wires and electrodes, or from other failure phenomena such as stiction and oxide growth. Thus, it is advantageous to have the sensor trace 101 present on the MEMS chip or on another chip in the same package so that early detection of oxidation can be achieved.

As previously mentioned and as discussed below, the sensor trace 101 is configured to oxidize more rapidly than the electrical component 103 on a MEMS chip in the same package. This oxidation can occur when moisture is present around the device. Moreover, any oxidation that is present within the device can be accelerated by a current that flows between the sensor trace 101 and the conductors 102, when sensor trace 101 is held at a more positive potential than conductor 102. As current flows, it leads to oxidation of the sensor trace 101, which can be detected by using an ohmmeter to measure the change in resistance of the sensor trace 101. As the sensor trace 101 oxidizes, its resistivity increases and eventually the sensor trace 101 is fully oxidized and the resistance jumps to a substantially higher resistance value.

In an exemplary embodiment, the sensor trace 101 may be narrow enough that partially oxidizing it substantially compromises its resistive or capacitive properties. The more narrower sensor trace 101 is, the more sensitive to oxidation it is. The state of the art for polysilicon wires used in MEMS devices is 1–2 microns. Thus, in a preferred embodiment, the device of the present invention will be oxidized most effectively if the sensor trace 101 is less than 2 microns in width. Although the sensor trace 101 is configured less than 2 microns in width in a preferred embodiment, it should be recognized that the sensor trace 101 may be configured at any width so long as it overall physical design allows it to oxidize prior to other wires in the system, thereby providing an early detection of package leakage.

The gap 104 between the sensor trace 101 and the conductor 102 may also affect the rate of oxidation, as it affects both the leakage current and the electric field (for a fixed potential drop between electrodes). For example, in one embodiment, the gap between the sensor trace 101 and the conductor 102 may be about 2 $\mu$m or less. However, a narrower gap 104 may operate to accelerate the rate of oxidation. Although FIG. 1A illustrates that the gap 104 is measured adjacent to the conductor 102, it should be noted that the gap 104 may also be measured vertically to another electrode or wire.

The oxidation sensor 100 may further include bonds pads 105 that can be connected to the sensor trace 101. While FIG. 1A illustrates the bond pads 105 connected directly to the sensor trace 101 with the electrical component 103, the bond pads 105 may also be connected to the sensor trace 101. One bond pad may be used to keep the sensor trace 101 at an elevated positive potential with respect to the conductor 102. A second bond pad may be used in conjunction with the first pad to measure resistance of the sensor trace 101. The bond pads 105 may be made of any conductive material.

In one exemplary embodiment, the conductor 102 is grounded; however, it is not necessary for purposes of the present invention that the conductor 102 be grounded in order that the sensor trace 101 oxidize before other wires or electrodes in the system. The sensor trace 101 is preferably configured to have a positive potential greater than a potential of the conductor 102 when a voltage is applied to the oxidation sensor 100. In such embodiments, as long as the conductor 102 is negative with respect to the sensor trace 101, the absolute potential of the conductor 102 does not matter.

In a particularly advantageous embodiment, the conductor 102 and the sensor trace 101 as illustrated in FIG. 1A are unpassivated. Because passivation inhibits oxidation, the sensor trace 101 and the conductor 102 are unpassivated in order to effectively oxidize. If the hermetic package within which the chip and oxidation sensor 100 are sealed were to leak, the resistance of sensor trace 101 would increase and be measured by the oxidation sensor 100 long before the electrical circuit or MEMS device itself would oxidize to the point of affecting performance or other failure phenomena begin to occur in the system. While the sensor trace 101 and the conductor 102 are unpassivated in advantageous embodiments, it should be noted that, unlike the sensor trace 101 and the conductor 102, the electrical component 103 may be passivated.

In environments with high voltage as well as high humidity, oxidation of poly-silicon wires and electrodes is especially observed. In one embodiment of the present invention, the oxidizing environment of the oxidation sensor 100 includes a relative humidity of greater than 50% and voltages of greater than 10 volts. When the MEMS chip is operated in these conditions, the most positively biased electrodes oxidize. While exemplary embodiments include a relative humidity of greater than 50% and voltages of greater than 10 volts, it should be recognized that other conditions of relative humidity and voltage that can cause an oxidizing environment are also included in the scope of the present invention.

It has been observed that relative humidity is an accelerating factor in the oxidation of the sensor trace 101 because the higher the humidity, the more water is absorbed on the insulation substrate between sensor trace 101 and conductor 102, which facilitates oxidation of the sensor trace 101. It is believed that the decomposition of water takes place and forms OH radicals that react with silicon in the presence of electrons and holes to form silicon oxide. The reaction governing anodic oxidation is:

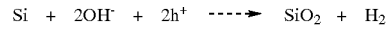
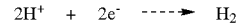

$$H_2O \longrightarrow H^+ + OH^-$$
$$Si + 2OH^- + 2h^+ \longrightarrow SiO_2 + H_2$$
$$2H^+ + 2e^- \longrightarrow H_2$$

As can be seen from the equation, only the positively biased electrode (supplying holes, labeled h) is oxidized, while the negatively biased electrode (supplying electrons, e) is unaffected. It is clear, at least from the above theoretical reaction equations, why the oxidation occurs at the positive electrode.

Figures 2A, 2B:
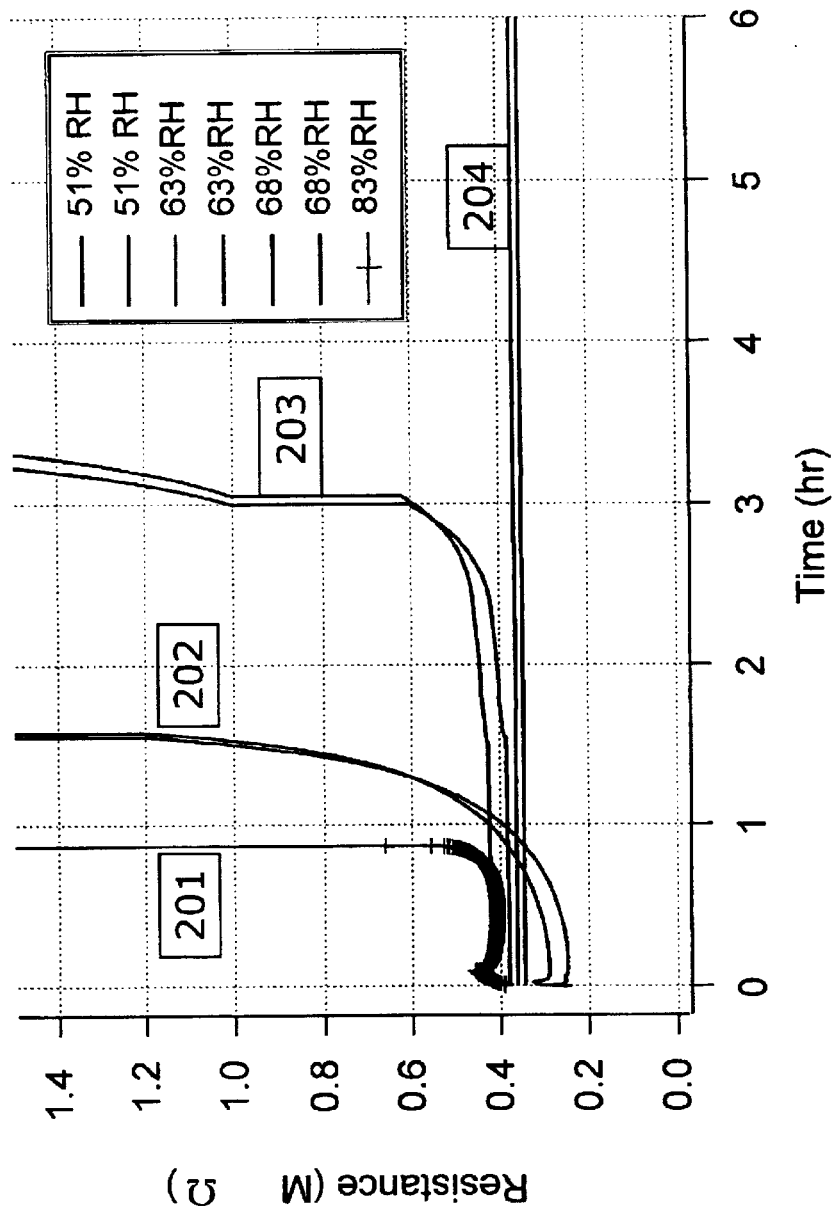
FIG. 2A is a plot of an oxidation sensor's resistance vs. time for 7 oxidation sensors of the present invention under different relative humidities.
FIG. 2B is a table of the time to fully oxidize an oxidation sensor of the present invention at 110 Volts for several relative humidities.

The effects of the presence of humidity within these devices is demonstrated in FIG. 2A. FIG. 2A is a plot of an oxidation sensor's resistance vs. time for 7 oxidation sensors constructed in accordance with the principles of the present invention under different relative humidities (RH). Two oxidation sensors are operated under 51% RH (204), two under 63% RH (203), two under 68% RH (202), and one oxidation sensor is operated under 83% RH (201). When humidity is present, the resistance increases over a period of time, and as shown in FIG. 2B, the higher the humidity, the quicker the complete oxidation of the sensor trace 101 and, thus, the time to open circuit. As illustrated in FIG. 2A, at 51% RH (204), the resistance does not increase over the test period, while at the higher humidities, the oxidation sensor becomes open circuits within hours. As noted in FIG. 2B, it takes more than 48 hours for an oxidation sensor at 51% RH to become an open circuit. On the other hand, it takes only 0.9 hours for an oxidation sensor at 83% RH to become an open circuit.

Figure 3:
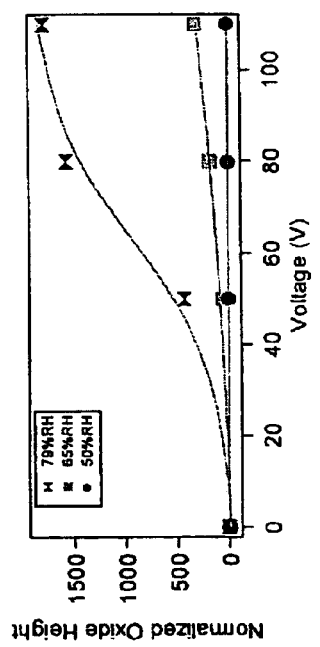
FIG. 3 graphically illustrates data regarding the amount of oxidation of a polysilicon sensor trace at various relative humidities and differing voltages.

FIG. 3 graphically illustrates data regarding the amount of oxidation of a polysilicon sensor trace after a 24 hour test at various relative humidities and differing voltages. As illustrated in FIG. 3, at a relative humidity of less than 50%, there is no measurable oxidation. However, at a relative humidity of 65%, the amount of oxidation begins to increase, and at a relative humidity of 79%, the amount of oxidation increases dramatically.

Figure 4:
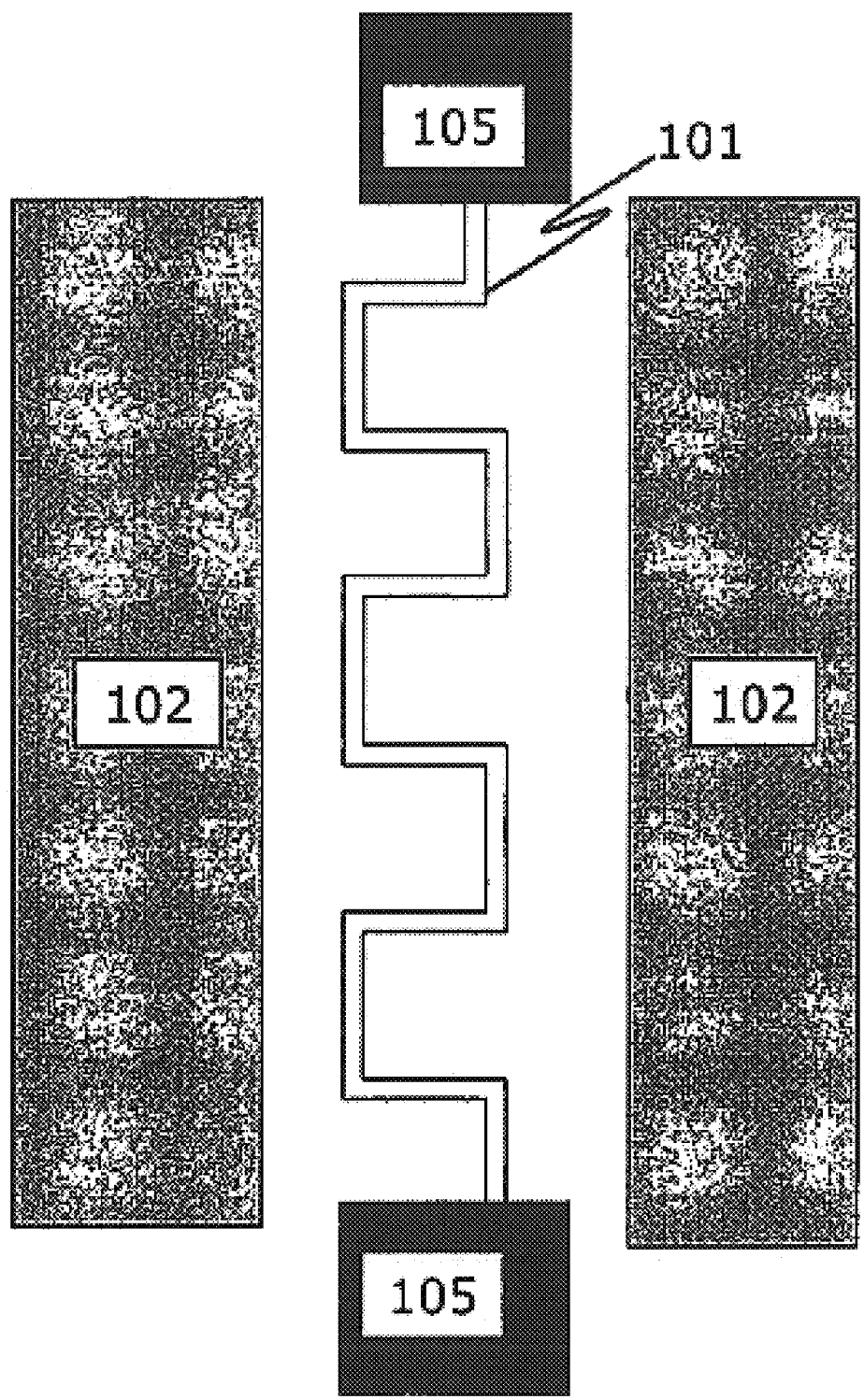
FIG. 4 illustrates a top view of one configuration of the present invention in which many 90° bends are constructed into the sensor trace.
Figure 5:
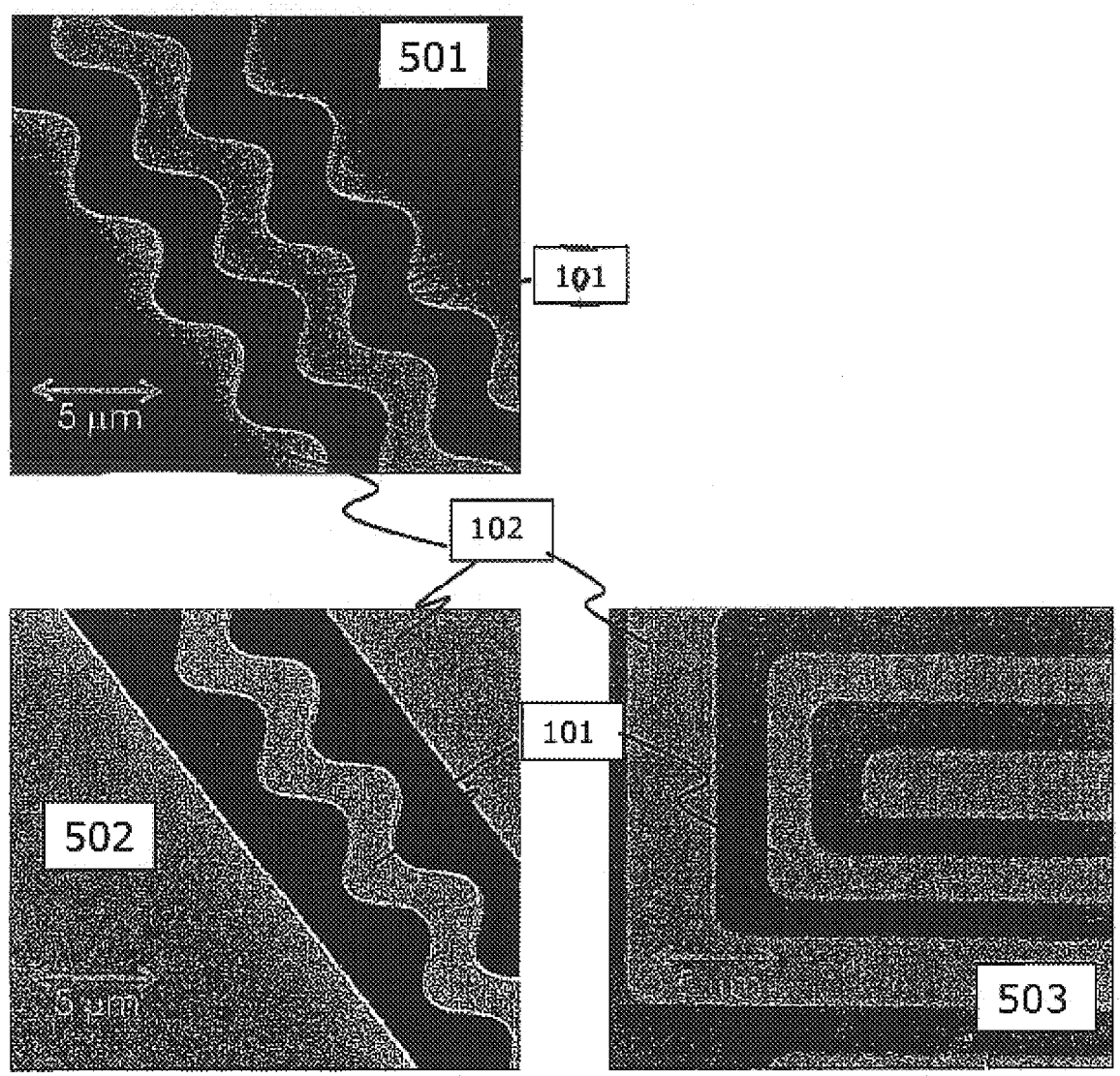
FIG. 5 illustrates three example structures that the oxidation sensor of the present invention may assume.

Turning now to FIG. 4, one advantageous embodiment of a serpentine configuration of the sensor trace 101 is illustrated. In this particular embodiment, the sensor trace 101 has a plurality of angled bends. The angled bends in the sensor trace 101 enhance the rate of oxidation, thereby providing a sensor trace that will oxidize even more rapidly than the other wires in the device. While the angled bends in FIG. 4 are 90° C., it should be understood that the angles of the sensor trace 101 may range from about 25° to about 175°. Although the most effective oxidation occurs in angles of 175°, a serpentine configuration of the sensor trace 101 that includes a pattern of angles of around 90° may be used because the oxidation sensor is more easily manufactured when the sensor trace 101 is shaped into 90° angles. While preferred embodiments include angles in the sensor trace 101, it should be understood that the sensor trace need not include angles in order to serve the purpose of sensing oxidation. For example, the sensor trace 101 may be configured in a straight line such as the sensor trace illustrated in FIG. 1A. Other alternative configurations are shown in FIG. 5.

The structure illustrated in 503, which includes a number of 90° angles, is an effective oxidation sensor. The angles that are included into the sensor trace 101 operate to sharpen the field lines and accelerate oxidation. The serpentine configurations of 502 and 501 are also effective oxidation sensors. In structure 501, both the sensor trace 101 and conductors 102 assume a serpentine configuration. In structure 502, the sensor trace 101 assumes a serpentine configuration while the conductor 102 assumes a straight configuration along the sensor trace 101. Thus, the sensor trace 101 may be shaped into any number of geometries and still be within the scope of the present invention.

Figure 6:
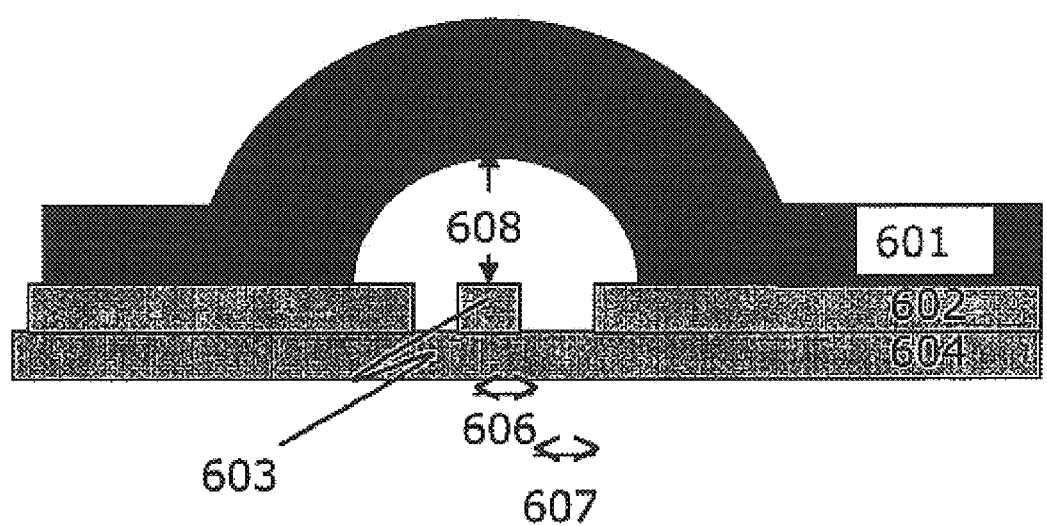
FIG. 6 illustrates a sectional view of the tunnel structure that the oxidation sensor of the present invention may assume where the oxidation sensor is capped by a grounded roof of poly-silicon.

FIG. 6 illustrates yet another structure that the oxidation sensor 100 may assume. FIG. 6 illustrates a cross section of the tunnel oxidation sensor. The sensor trace 603 and the conductor 602 are capped by a roof layer 601. In an advantageous embodiment, the roof layer is a grounded roof layer of polysilicon. As previously mentioned, the width of the sensor trace 606 and the width of the space between the sensor trace 603 and the conductor 602 may be narrow in order to facilitate oxidation. Beneath the sensor trace 603 and conductor 602 is a bottom layer 604. Any generic insulator may be used to construct the bottom layer 604. For example, silicon nitride may be included in the bottom layer 604. In another advantageous embodiment, the height 608 of the grounded roof of polysilicon 601 is as close to the sensor trace 603 as possible, which facilitates oxidation. It should be noted that there are a number of types of different tunnel oxidation sensors that may be configured by adjusting the height 608 of the grounded roof of polysilicon 601 in relation to the sensor trace 603, as well as adjusting other parameters of the tunnel oxidation sensor. The order in which the structures of FIG. 5 become open circuits for given relative humidities and bias voltages (and thus serve as more effective oxidation sensors) is 503 of FIG. 5, the tunnel structure of FIG. 6, 502 of FIG. 5 and 501 of FIG. 5.

Figure 7:
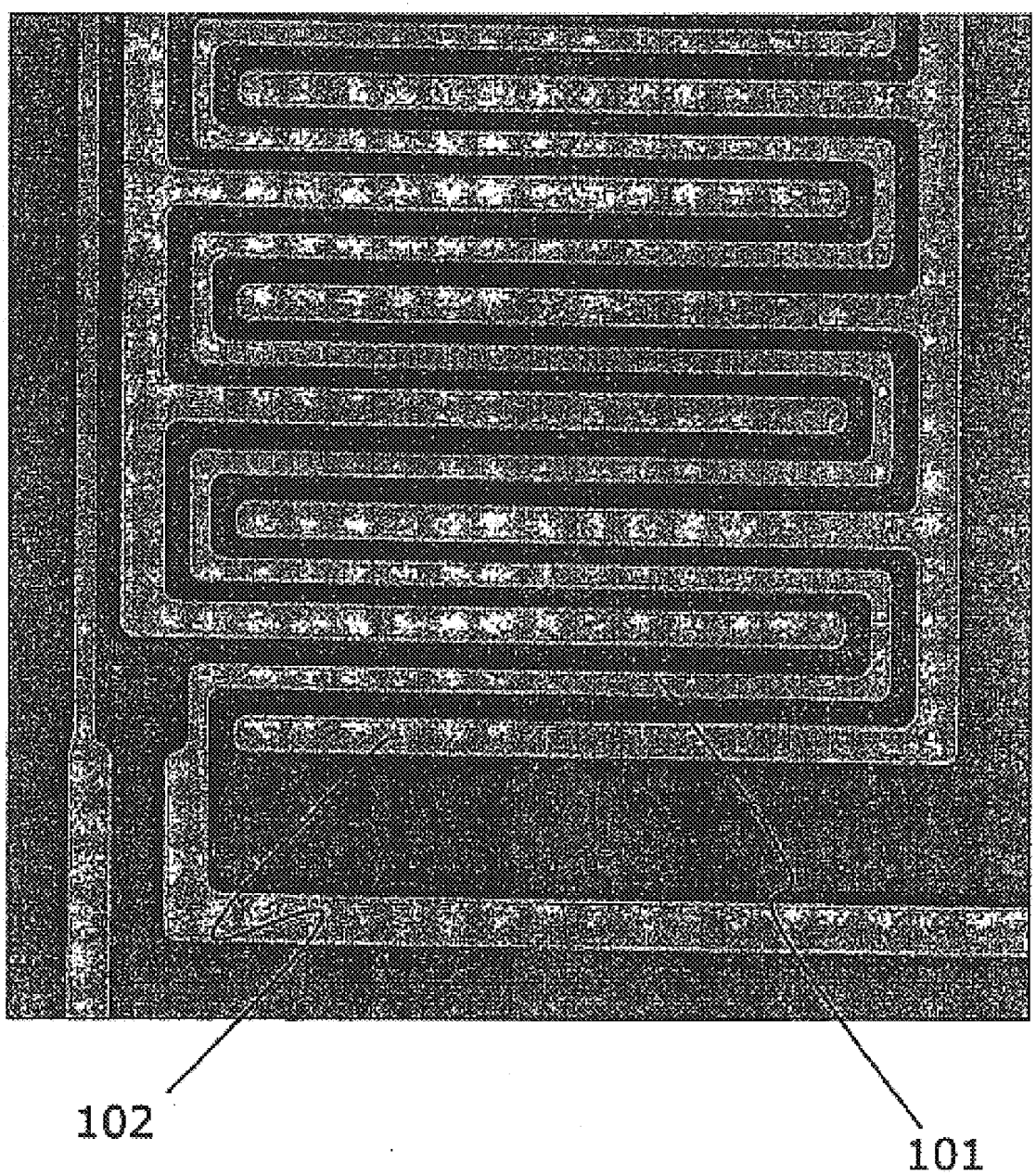
FIG. 7 illustrates a top view of an unused sensor trace and conductors.
Figure 8:
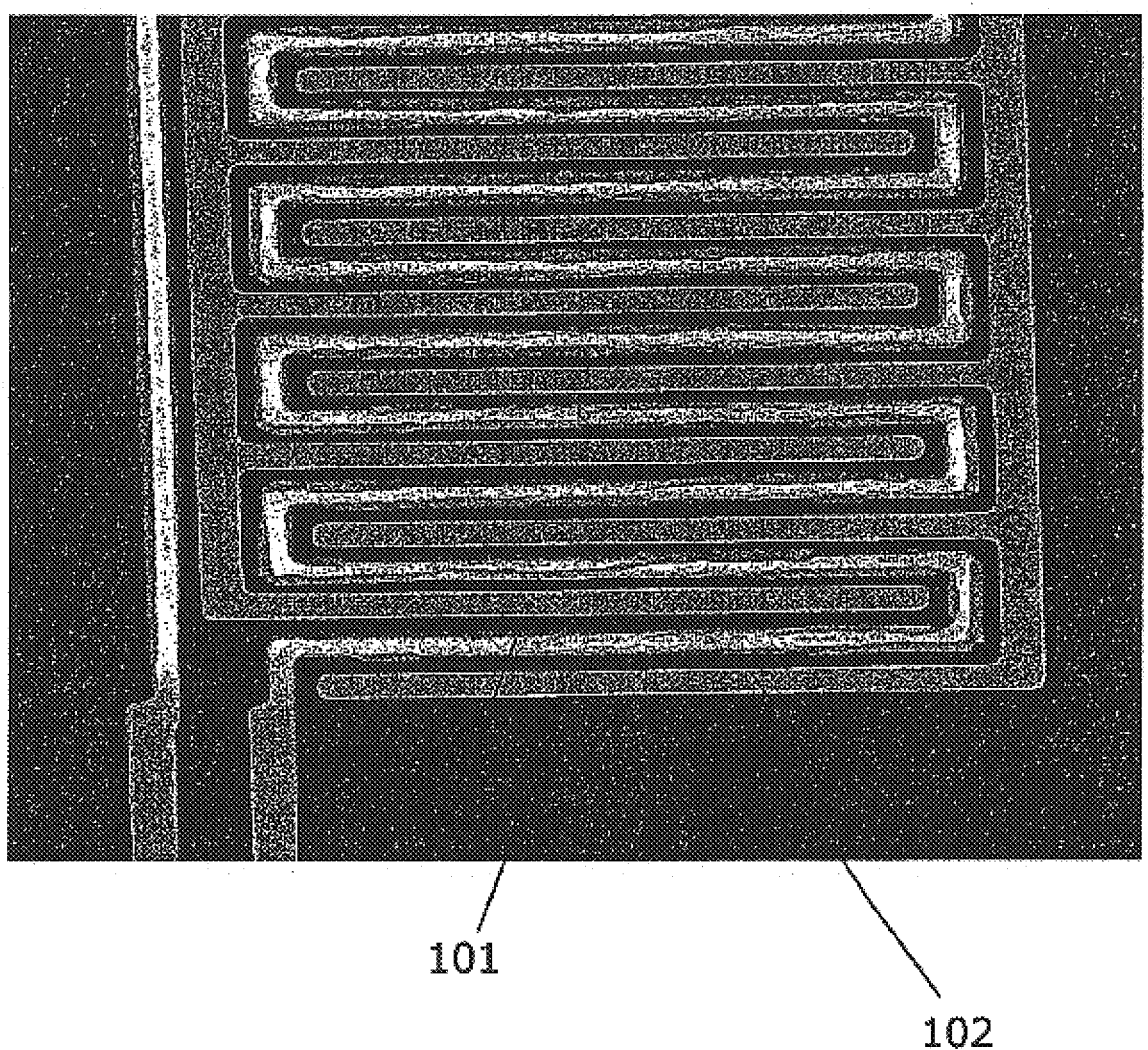
FIG. 8 illustrates a top view of an oxidized sensor trace 101 after 4 hours at 60% RH and +110V.

Turning now to FIGS. 7 and 8, illustrated is the effects of anodic oxidation on oxidation sensor 100. FIG. 7 is a top view of an unused sensor trace 101 and conductors 102. In comparison, FIG. 8 is an image of the sensor trace 101 and conductors 102 after 4 hours at 60% RH and +110 Volts. As illustrated in FIG. 8, the sensor trace 101 is very oxidized indicated by areas 101, while the grounded conductors 102 are substantially unoxidized. Due to the amount of oxidation, the sensor trace 101 in FIG. 8 is electrically an open circuit.

Figure 9:
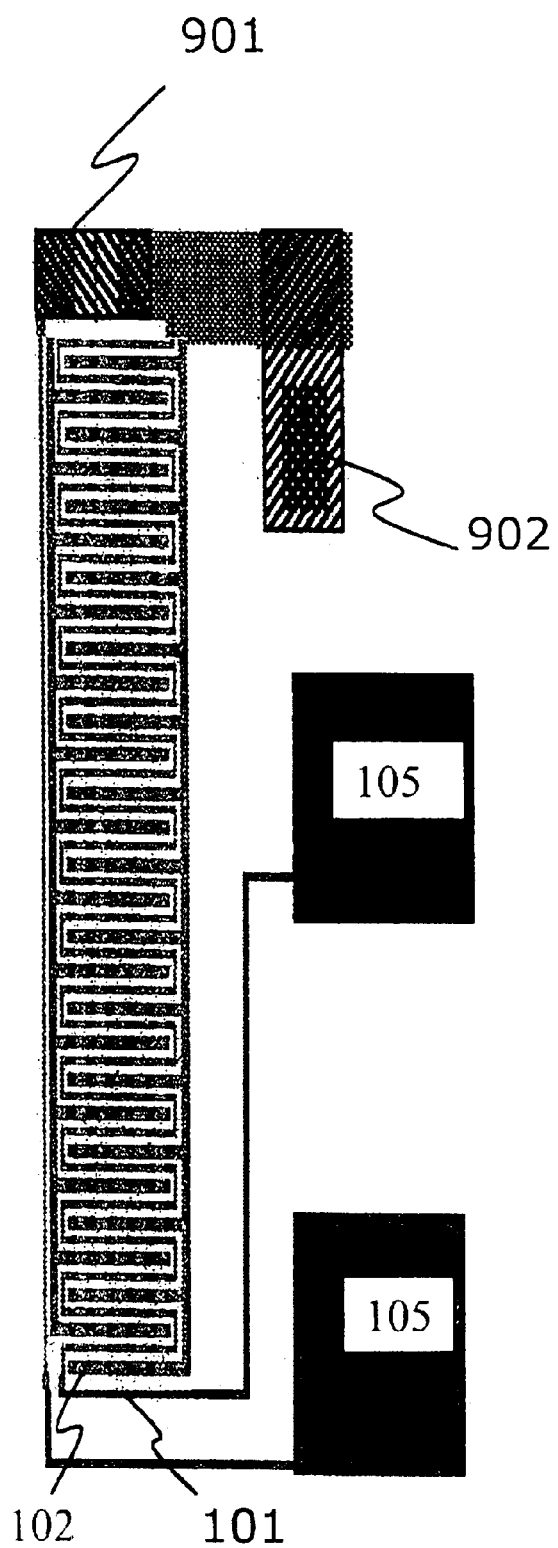
FIG. 9 is a top view of a non-tunnel, style A oxidation sensor illustrating a connector being used to connect the grounded conductor to a ground contact via.

FIG. 9 is a top view of the configuration 503 illustrated in FIG. 5. A connector 901 is used to connect the grounded conductor 102 to the ground contact via 902. The sensor trace 101 is connected to the bond pads 105. While FIG. 9 illustrates a connector 901 that is used to connect the grounded conductor 102 to the ground contact via 902, the connector 901 is not necessary to connect the oxidation sensor system. For example, the grounded conductor 102 may be connected to the ground contact via 902 directly.

Figure 10:
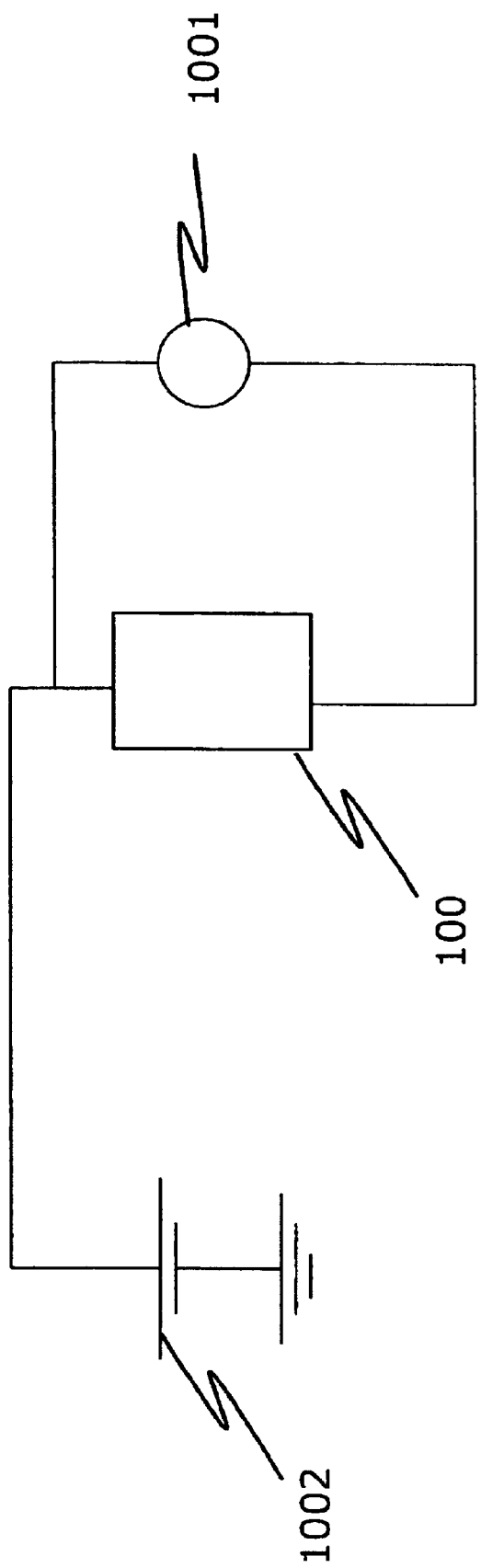
FIG. 10 illustrates one way that the sensor trace may be electrically connected so that it anodically oxidizes.

FIG. 10 simply illustrates an advantageous electrical configuration in which the present invention may be incorporated. The potential drop to drive the possible anodic oxidation of the oxidation sensor 100 is supplied by a dc voltage supply 1002. As the oxidation sensor anodically oxidizes, the resistance of the wire increases, and this increase is readily measured using a floating ohmmeter 1001. While the package may be initially hermetically sealed, if the seal is broken and the internal wiring is exposed to moisture, the resistance of the sensor trace rises with time. This advanced warning allows the user to know the package has a problem well before the occurrence of failure phenomena, such as stiction or oxide growth, which cause failure in the system (for example, in a MEMS device, the moving parts can no longer be made to move). The resistance of the oxidation sensor 100 provides a direct measure of the amount of sensor trace 101 that has been anodically oxidized. An ac monitoring system can also be used to measure the resistance of the sensor trace using a small ac probe voltage while the large dc voltage is still applied to one side of the sensor trace. While an ac monitoring system may be used to measure the resistance of the sensor trace, it should be understood that any voltage measuring technique of sufficient sensitivity can be used to measure the changes in system's resistance or voltage. For example, the user may also measure the current flowing from the sensor trace 101 to the surrounding conductors 102 and use that as an indirect measure of how much oxidation has occurred.

It should be understood that there can be any number of sub-chips of oxidation sensors included in a chip. Moreover, there can be any number of different oxidation sensor combinations of the non-tunnel configurations of FIG. 5 and the tunnel configuration of FIG. 6.

Although the present invention has been described in detail, those skilled in the art should understand that they can make various changes, substitutions and alterations herein without departing from the spirit and scope of the invention in its broadest form.

What is claimed is:

1. An oxidation sensor for an electrical circuit, comprising:
   at least two conductors located on an insulating substrate;
   a sensor trace located on the insulating substrate and located between the at least two conductors, wherein the sensor trace is configured to have a positive potential greater than a potential of the at least two conductors when a voltage is applied to the sensor trace;
   an oxidizable electrical component associated with the sensor trace, wherein the sensor trace is configured to oxidize at a rate greater than the electrical component when the sensor trace and the electrical component are exposed to a same oxidizing environment; and
   wherein the oxidation sensor is capped by a grounded roof layer.

2. The oxidation sensor as recited in claim 1 wherein the sensor trace is configured to have a positive potential greater than a potential of the at least two conductors in the presence of an applied voltage.

3. The oxidation sensor as recited in claim 1 wherein the sensor trace is located a distance from the at least two conductors of about 2 $\mu$m or less.

4. The oxidation sensor as recited in claim 1 wherein the at least two conductors are grounded.

5. The oxidation sensor as recited in claim 1 wherein the sensor trace comprises a conductive material selected from the group consisting of:
   titanium,
   copper,
   tungsten,
   aluminum, and
   tantalum.

6. The oxidation sensor as recited in claim 1 wherein the sensor trace comprises silicon.

7. The oxidation sensor as recited in claim 1 further including bonds pads connected to the sensor trace.

8. The oxidation sensor as recited in claim 1 wherein the sensor trace has a serpentine configuration.

9. The oxidation sensor as recited in claim 8 wherein the serpentine configuration includes a pattern of angles.

10. The oxidation sensor as recited in claim 9 wherein the angles range from about 25 degrees to about 175 degrees.

11. The oxidation sensor as recited in claim 1 wherein the sensor trace and the at least two conductors have a serpentine configuration.

12. The oxidation sensor as recited in claim 1 wherein the sensor trace is unpassivated.

13. The oxidation sensor as recited in claim 1 wherein the oxidizing environment includes a relative humidity of greater than 50% and voltages of greater than 10 volts.

14. The oxidation sensor as recited in claim 1 wherein the sensor trace has a width less than 2 microns.

15. A method of manufacturing an oxidation sensor for an electrical circuit, comprising:

forming at least two conductors on an insulating substrate; and forming a sensor trace located on the insulating substrate and located between the at least two conductors, wherein the sensor trace is configured to have a positive potential greater than a potential of the at least two conductors when a voltage is applied to the sensor trace;

associating an oxidizable electrical component with the sensor trace, wherein the sensor trace is configured to oxidize at a rate greater than the electrical component when the sensor trace and the electrical component are exposed to a same oxidizing environment and wherein the oxidation sensor is capped by a grounded roof layer.

16. The method as recited in claim 15 wherein forming the sensor trace includes forming the sensor trace so that the sensor trace is located at a distance from the at least two conductors of about 2 $\mu$m or less.

17. The method as recited in claim 15 wherein forming the at least two conductors includes forming grounded conductors.

18. The method as recited in claim 15 wherein forming the sensor trace includes forming the sensor trace so that the sensor trace comprises a conductive material selected from the group consisting of:

titanium, copper, tungsten, aluminum, and tantalum.

19. The method as recited in claim 15 wherein forming the sensor trace includes forming the sensor trace so that the sensor trace comprises silicon.

20. The method as recited in claim 15 wherein forming a sensor trace includes forming bonds pads connected to the sensor trace.

21. The method as recited in claim 15 wherein forming the sensor trace includes forming the sensor trace with a serpentine configuration.

22. The method as recited in claim 21 wherein forming the sensor trace with a serpentine configuration includes forming a pattern of angles.

23. The method as recited in claim 22 wherein forming a pattern of angles includes forming a pattern of angles so that the angles range from about 25 degrees to about 175 degrees.

24. The method as recited in claim 15 wherein forming the sensor trace and the at least two conductors include forming the sensor trace and the at least two conductors include forming them into a serpentine configuration.

25. The method as recited in claim 15 wherein forming the sensor trace includes forming an unpassivated sensor trace.

26. The method as recited in claim 15 wherein exposing the sensor trace and the electrical component to an oxidizing environment includes a relative humidity of greater than 50% and voltages of greater than 10 volts.

27. The method as recited in claim 15 wherein forming the sensor trace includes forming the sensor trace such that a width of the sensor trace is less than 2 microns.

28. A micro-electromechanical device, comprising:

an actuator;

an actuation mechanism;

an oxidizable electrical component; and an oxidation sensor, comprising:

at least two conductors located on an insulating substrate;

a sensor trace located on the insulating substrate and located between the at least two conductors, wherein the sensor trace is configured to have a positive potential greater than a potential of the at least two conductors when a voltage is applied to the sensor trace and configured to oxidize at a rate greater than the electrical component trace when the sensor trace and the electrical component are exposed to a same oxidizing environment and wherein the oxidation sensor is capped by a rounded roof layer.

29. The oxidation sensor as recited in claim 28 wherein the sensor trace is located a distance from the at least two conductors of about 2 $\mu$m or less.

30. The oxidation sensor as recited in claim 28 wherein the at least two conductors are grounded.

31. The oxidation sensor as recited in claim 28 wherein the sensor trace comprises a conductive material selected from the group consisting of:

titanium, copper, tungsten, aluminum, and tantalum.

32. The oxidation sensor as recited in claim 28 wherein the sensor trace comprises silicon.

33. The oxidation sensor as recited in claim 28 further including bonds pads connected to the sensor trace.

34. The oxidation sensor as recited in claim 28 wherein the sensor trace has a serpentine configuration.

35. The oxidation sensor as recited in claim 34 wherein the serpentine configuration includes a pattern of angles.

36. The oxidation sensor as recited in claim 35 wherein the angles range from about 25 degrees to about 175 degrees.

37. The oxidation sensor as recited in claim 28 wherein the sensor trace and the at least two conductors have a serpentine configuration.

38. The oxidation sensor as recited in claim 28 wherein the electrical component and the sensor trace are unpassivated.

39. The oxidation sensor as recited in claim 28 wherein the oxidizing environment includes a relative humidity of greater than 50% and voltages of greater than 10 volts.

40. The oxidation sensor as recited in claim 28 wherein the sensor trace has a width less than 2 microns.

* * * * *